(12) United States Patent
Uribe et al.

(10) Patent No.: US 9,226,776 B2
(45) Date of Patent: Jan. 5, 2016

(54) APPARATUS FOR OCCIPITAL-CERVICAL FIXATION ENABLING SUPPLEMENTAL OCCIPITAL BONE FIXATION

(71) Applicant: UNIVERSITY OF SOUTH FLORIDA, Tampa, FL (US)

(72) Inventors: Juan S. Uribe, Tampa, FL (US); Wesley M. Johnson, Gainesville, FL (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 14/064,834

(22) Filed: Oct. 28, 2013

(65) Prior Publication Data

US 2014/0052188 A1    Feb. 20, 2014

Related U.S. Application Data

(63) Continuation of application No. 12/742,411, filed as application No. PCT/US2008/085154 on Dec. 1, 2008, now Pat. No. 8,568,459.

(60) Provisional application No. 60/990,987, filed on Nov. 29, 2007.

(51) Int. Cl.
*A61B 17/56* (2006.01)
*A61B 17/70* (2006.01)

(52) U.S. Cl.
CPC ......... *A61B 17/7002* (2013.01); *A61B 17/7055* (2013.01)

(58) Field of Classification Search
CPC .................. A61B 17/7055; A61B 17/6433
USPC .......................... 606/246, 264–279
See application file for complete search history.

(56) References Cited

U.S. PATENT DOCUMENTS

| | | | |
|---|---|---|---|
| 5,360,429 A | 11/1994 | Jeanson et al. | |
| 5,545,164 A | 8/1996 | Howland | |
| 5,582,612 A | 12/1996 | Lin | |
| 6,146,382 A | 11/2000 | Hurlbert | |
| 7,232,441 B2 | 6/2007 | Altarac et al. | |
| 7,618,443 B2 | 11/2009 | Abdou | |
| 7,901,433 B2 * | 3/2011 | Forton et al. ................. | 606/250 |

(Continued)

FOREIGN PATENT DOCUMENTS

WO    WO-2007/084900 A2    7/2007

OTHER PUBLICATIONS

International Search Report in International Application No. PCT/US2008/085154, filed Dec. 1, 2008.

*Primary Examiner* — Mary Hoffman
(74) *Attorney, Agent, or Firm* — Saliwanchik, Lloyd & Eisenschenk

(57) ABSTRACT

An apparatus for stabilization of a patient's head relative to the patient's neck joint includes an occi-cervical base member having a "C"-shaped central part and first and second attachment rods respectively connected to and extending transversely from free ends of the central part. An occiput attachment has a first end slideably engaged to the central part and a flat, straight second end that extends radially outwardly relative to the first end. First and second polyaxial screw heads are adapted to be implanted in first and second occipital condyles of a patient, respectively. The first and second polyaxial screw heads are adapted to engage first and second stabilizing rods, respectively, that are placed in-line with the cervical spine of a patient and to engage the first and second attachment rods, respectively.

12 Claims, 3 Drawing Sheets

(56) References Cited

U.S. PATENT DOCUMENTS

| | | |
|---|---|---|
| 8,007,499 B2 | 8/2011 | Piehl |
| 8,083,743 B2 | 12/2011 | Henderson et al. |
| 8,870,918 B2 * | 10/2014 | Boomer et al. ............... 606/246 |
| 8,900,276 B2 * | 12/2014 | Purcell et al. ................ 606/280 |
| 2005/0080417 A1 | 4/2005 | Alexis et al. |
| 2005/0124994 A1 | 6/2005 | Berger et al. |
| 2005/0283153 A1 | 12/2005 | Poyner et al. |
| 2005/0288669 A1 * | 12/2005 | Abdou ............................ 606/61 |
| 2006/0004363 A1 | 1/2006 | Brockmeyer et al. |
| 2006/0217710 A1 * | 9/2006 | Abdou ............................ 606/54 |
| 2007/0233119 A1 | 10/2007 | Markworth |
| 2007/0270809 A1 * | 11/2007 | Drewry et al. ................. 606/61 |
| 2008/0051783 A1 * | 2/2008 | Null et al. ...................... 606/61 |
| 2010/0121384 A1 | 5/2010 | Abdou |
| 2014/0052181 A1 * | 2/2014 | Lemoine ...................... 606/246 |

\* cited by examiner

APPARATUS FOR OCCIPITAL-CERVICAL FIXATION ENABLING SUPPLEMENTAL OCCIPITAL BONE FIXATION

CROSS-REFERENCE TO RELATED APPLICATION

This application is a continuation of U.S. application Ser. No. 12/742,411, filed Sep. 13, 2010, now U.S. Pat. No. 8,568,459, issued Oct. 29, 2013, which is the U.S. national stage application of International Patent Application No. PCT/US2008/085154, filed Dec. 1, 2008, which claims the benefit of U.S. Provisional Application No. 60/990,987, filed Nov. 29, 2007, all of which are hereby incorporated by reference in their entirety.

FIELD OF THE INVENTION

This invention relates to medical treatments. More particularly, it relates to an apparatus that enables stabilization of the upper cervical spine with occipital condyle screws and a base member for holding the screws.

BACKGROUND

The medical treatments heretofore known that relate to stabilization of the upper cervical spine are limited by poor occipital bone purchase and multiple attachment points for screws with subsequent construct failure at the cranio-cervical junction. Conventional systems for providing more reliable stabilization of the head to the neck joint rely on attachment from the neck to the back of the skull. However, in some cases the back of the skull (occiput) is unsuitable for attaching existing rigid plates and rods. For example, when suboccipital craniectomy has been performed there is no occipital bone available to which connections for stabilization can be made. Moreover, the known upper cervical spine stabilization systems use rather long, contoured rods that need to be contoured in the operating room. Such rods are subject to failure due to large bending forces.

There is therefore a need for a medical treatment that optimizes bone fusion/fixation at the occipito-cervical junction by creating a more rigid biomechanical construct that has a lower profile and can be used as a supplement or alternative to conventional fixation methods.

More particularly, there is a need for a method that eliminates the long, contoured rods.

Occipito-cervical fusion is indicated when the cranio-cervical junction is rendered unstable by various disease processes. Over the past decade, rigid fixation of the occiput using plate-screw or rod constructs with screw fixation has become popular. To increase the rigidity of the different available constructs, and due to the poor occipital bone purchase, multiple attachment points at the occiput are required. The variable regional bone thickness of the occiput, combined with the location of the dural sinuses, limits the placement and length of occipital screws, thus potentially affecting construct strength and rigidity. The optimal placement of screws in the occipital bone is technically demanding and in cases where suboccipital craniectomy is performed the area available for hardware placement is even more restricted.

Thus there is a need for an improved apparatus that does not require rigid fixation of the occiput using plate-screw or rod constructs with screw fixation.

There is also a need for a system that does not require multiple attachment points at the occiput.

However, in view of the prior art taken as a whole at the time the present invention was made, it was not obvious to those of ordinary skill how the identified needs could be fulfilled.

SUMMARY OF THE INVENTION

The long-standing but heretofore unfulfilled need for an improved, more reliable medical apparatus for stabilization of the head to the neck joint is now met by a new, useful, and non-obvious invention that eliminates the long, contoured rods of the prior art, the rigid fixation of the occiput using plate-screw or rod constructs with screw fixation, and multiple attachment points at the occiput.

To overcome the prior art shortcomings of poor occipital bone purchase and multiple attachment points with subsequent construct failure, this disclosure teaches occipito-cervical fusion employing fixation of the occipital condyle that incorporates the occipital bone and the C1/C2 levels with a polyaxial screw rod construct. An implementation of the invention includes polyaxial screws that are implanted individually in the occipital condyles and a connecting polyaxial crosslink with attachments that incorporate attachment to the occipital bone into the construct. The invention addresses the potential hardware failure due to poor occipital bone purchase and limited points of fixation obtained with occipital bone screws only.

The inventive structure is a novel apparatus for stabilization of a patient's head relative to the patient's neck joint. An embodiment of the structure includes an occi-cervical base member having a "C"-shaped central part that includes a pair of transversely spaced apart free ends. A first attachment rod is connected to and extends transversely from a first free end of the pair of free ends. A second attachment rod is connected to and extends transversely from a second free end of the pair of free ends.

An occiput attachment has a first end slideably engaged to the "C"-shaped central part. A flat, straight second end extends radially outwardly relative to the first end.

A first polyaxial screw head is adapted to be implanted in a first occipital condyle of a patient and a second polyaxial screw head is adapted to be implanted in a second occipital condyle of the patient. The first and second polyaxial screw heads are adapted to engage first and second stabilizing rods, respectively, that are placed in-line with the cervical spine of the patient. The first and second polyaxial screw heads are also adapted to engage the first and second attachment rods, respectively. The first and second attachment rods can be rigid and are disposed at a ninety degree (90°) angle relative to the first and second stabilizing rods. This achieves occipito-cervical fusion employing fixation of the occipital condyle that incorporates the occipital bone and the C1/C2 levels. Hardware failure due to poor occipital bone purchase and limited points of fixation with occipital bone screws can thus be avoided.

According to an embodiment, each of the polyaxial screw heads has two grooves disposed at a ninety degree (90°) angle relative to one another. The two grooves include a first groove that is deeper than a second groove. The first groove is adapted to accommodate the first stabilizing rod that is placed in-line with a cervical spine and the second groove is adapted to accommodate the attachment rod.

A saddle accommodates and secures both the stabilizing rod and the occi-cervical attachment rod within the polyaxial screw head.

In one embodiment, the occi-cervical attachment rods are polyaxial. A plurality of locking set screws are provided to secure the polyaxial attachment rods in a preselected configuration.

According to an implementation of the invention, at least one occiput attachment means has a first end slideably connected to the occi-cervical base member and a flat, straight second end that extends radially relative to the first end. At least one aperture is formed in the flat second end and is adapted to receive a screw that secures the attachment means to a patient's occiput.

According to the implementation, the first end of the occiput attachment means has a set-screw-receiving aperture formed therein so that a user may secure the occiput attachment means to the occi-cervical base member at any position of functional adjustment from among an infinite number of positions of functional adjustment along the length of the occi-cervical base member.

A broad object of the invention is to provide an apparatus that optimizes bone fusion/fixation at the occipito-cervical junction by creating a more rigid biomechanical construct that has a lower profile and can be used as a supplement or alternative to conventional fixation methods.

Another object is to provide an improved apparatus that does not require rigid fixation of the occiput using plate-screw or rod constructs with screw fixation.

Still another object is to provide an apparatus that does not require multiple attachment points at the occiput.

Another important object of the invention is to achieve stabilization of the upper cervical spine with occipital condyle screws and a base member for holding the screws.

Another important object is to achieve said stabilization even when the attachment points are limited by poor occipital bone purchase.

It is also an important object to achieve the foregoing objects in the absence of elongate, contoured rods.

These and other important objects, advantages, and features of the invention will become clear as this description proceeds.

The invention accordingly comprises the features of construction, combination of elements, and arrangement of parts that will be exemplified in the description set forth hereinafter and the scope of the invention will be indicated in the claims.

BRIEF DESCRIPTION OF THE DRAWINGS

For a fuller understanding of the nature and objects of the invention, reference should be made to the following detailed description, taken in connection with the accompanying drawings, in which.

DETAILED DESCRIPTION OF THE PREFERRED EMBODIMENT

Embodiments of the present invention relate to stabilization of the upper cervical spine. In particular, embodiments of the present invention provide an apparatus and method for stabilization of a head to a neck joint.

In accordance with an embodiment of the present invention, an apparatus for stabilization of the upper cervical spine is provided having a structure that includes three main parts. The first part can be referred to as a base, the second part can be referred to as an occiput attachment, and the third part can be referred to as a polyaxial screw.

Figure 1:
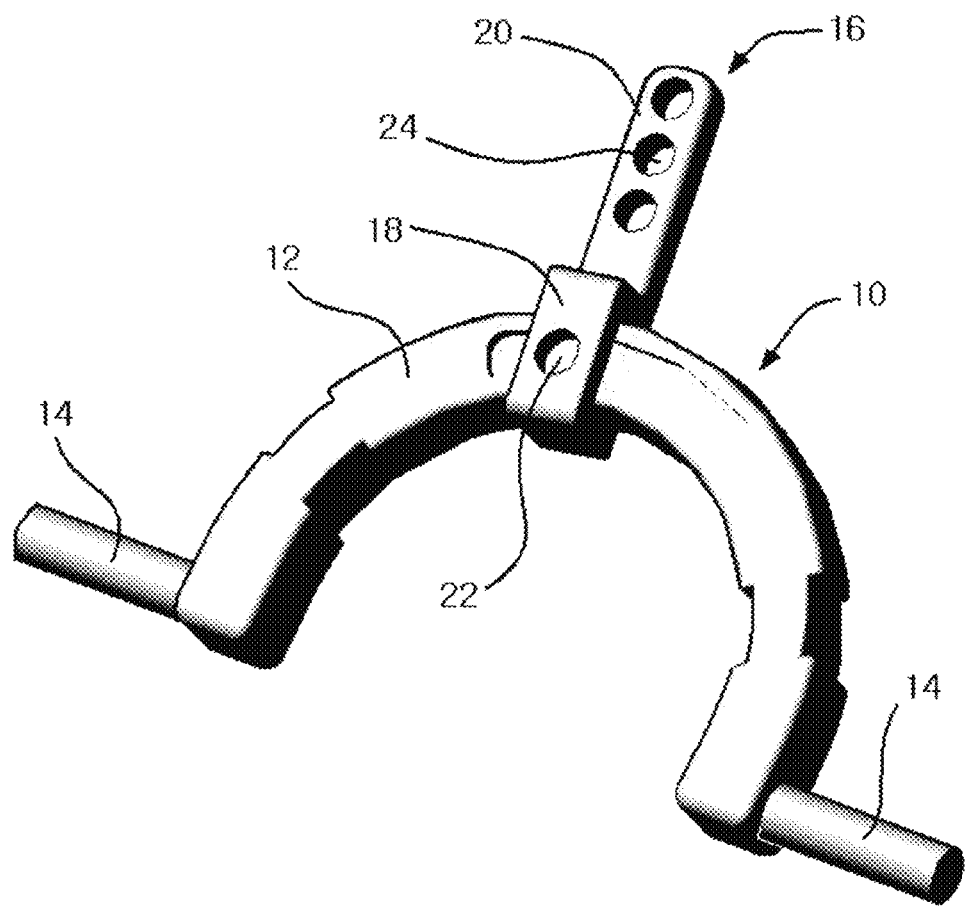
FIG. 1 is a perspective view of the assembly of an occi-cervical base and one occiput attachment.

Referring first to FIG. 1, it will there be seen that the first main part can be a rigid occi-cervical base member, denoted 10 as a whole. Base 10 includes "C"-shaped central part 12 and a pair of rigid attachment rods, collectively denoted 14, that extend transversely outwardly at respective free ends of said "C"-shaped occi-cervical central part. The occi-cervical base member can be a plate or crosslink.

The second main part, also depicted in FIG. 1, is occiput attachment 16 having a first end 18 that slideably engages "C"-shaped central part 12 and a flat, straight second end 20 that extends radially from said first end 18. A set screw-receiving aperture 22 is formed in said first end 18 so that occiput attachment 16 may be secured to central part 12 by a set screw in a surgeon-selected position from among an infinite number of positions of functional adjustment along the extent of said central part 12.

A plurality of screw-receiving apertures, collectively denoted 24, are formed in the flat second end 20. Occiput attachment 16 connects occi-cervical base 10 to the occiput of a patient with suitable fastening means such as screws that can be selectively received within said apertures 24. More than one occiput attachment 16 may be used in an application. Their application and number are determined by the surgeon through surgical planning and intraoperatively.

Figure 2:
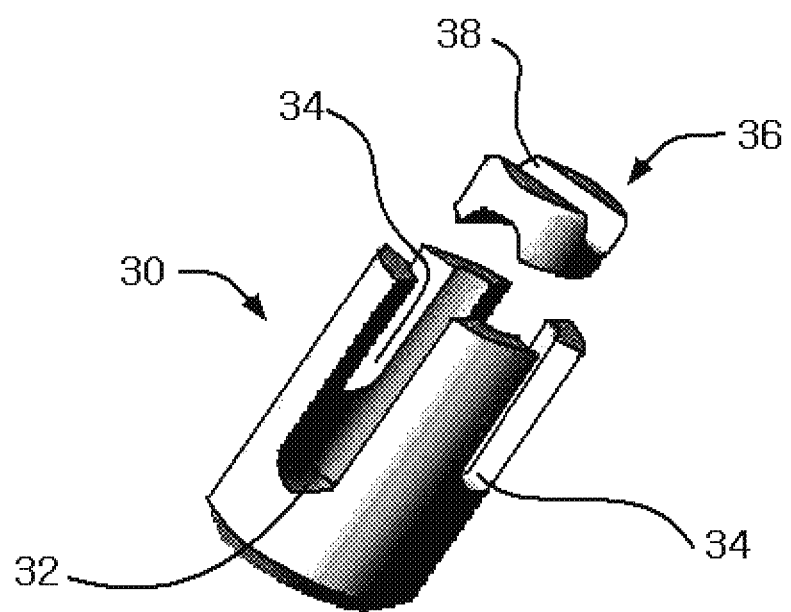
FIG. 2 is a perspective view of the novel polyaxial screw (C0 condyle) with inter-rod saddle.

As depicted in FIG. 2, the third main part can be a special polyaxial screw head 30 adapted to be attached to the occipital condyles of a patient. In practice, two (2) of these special screws are used, i.e., one for each occipital condyle. The screws and/or screw presser saddle used with the subject screw head can be any suitable screw known in the art. As shown in FIG. 2, the subject screw head 30 has two intersecting grooves 32, 34 of differing depths disposed at ninety degree (90°) angles relative to one another. A first type groove 32 has a depth greater than a depth of a second type groove 34.

The first type groove 32 accommodates a stabilizing rod, not depicted, that is placed in-line with the cervical spine of a patient and other polyaxial or fixed axis screws in the lateral vertebral bodies of the upper cervical spine. The extent of the cervical spine to which the rods and screws are attached is a matter of surgeon judgment.

Figure 3:
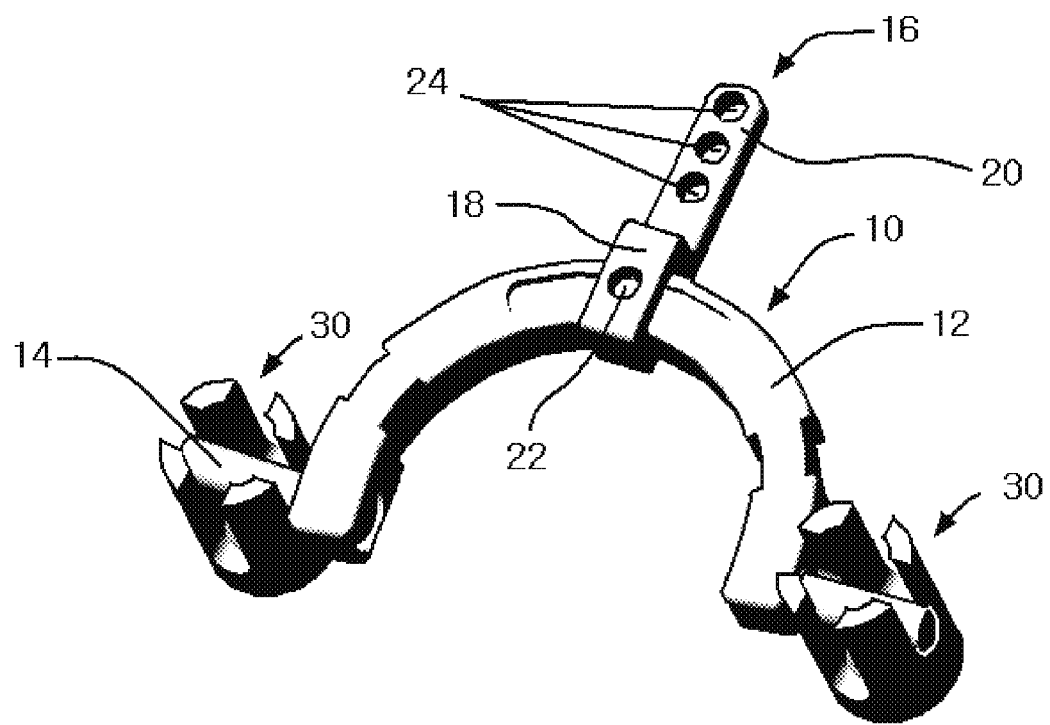
FIG. 3 is a perspective view of an assembly of the occi-cervical base and occiput attachment of FIG. 1 and the polyaxial screw head of FIG. 2.

As shown in FIG. 3, the second type groove 34 accommodates its associated attachment rod 14. Thus, each attachment rod 14 overlies a stabilizing rod (not shown) positioned in the first type groove 32 and said rods are disposed in ninety degree (90°) intersecting relation to one another.

One polyaxial screw head 30 is adapted to be implanted in a first occipital condyle of a patient and a second polyaxial screw head 30 is adapted to be implanted in a second occipital condyle of the patient. The two polyaxial screw heads 30 are adapted to engage first and second stabilizing rods (not shown), respectively, that are placed in-line with the cervical spine of the patient. The two polyaxial screw heads 30 are also adapted to respectively engage the two attachment rods 14 that transversely extend from the occipital base member 10. The two attachment rods 14 can be disposed at a ninety degree (90°) angle relative to the first and second stabilizing rods, respectively. This achieves occipito-cervical fusion employing fixation of the occipital condyle that incorporates the occipital bone and the C1/C2 levels. Accordingly, hardware failure due to poor occipital bone purchase and limited points of fixation with occipital bone screws can be avoided.

Referring back to FIG. 2, an inter-rod saddle 36 can be further included. Inter-rod saddle 36 has a tool-engageable head 38 and is adapted to secure stabilizing rod and attachment rod 14 within grooves 32 and 34, respectively, of screw 30.

The attachment rods 14 can be rigid or polyaxial. Locking set screws can secure the polyaxial attachment rods in a desired configuration where the attachments are polyaxial. That configuration is determined intraoperatively by the surgeon.

It will thus be seen that the objects set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

What is claimed is:

1. An apparatus for stabilization of a patient's head relative to the patient's neck joint, comprising:
    an occi-cervical base member having a "C"-shaped central part that includes a pair of transversely spaced apart free ends;
    a first attachment rod connected to and extending transversely from a first free end of the pair of free ends;
    a second attachment rod connected to and extending transversely from a second free end of the pair of free ends;
    an occiput attachment having a first end engaged to the "C"-shaped central part and a flat, straight second end that extends radially outwardly relative to the first end;
    wherein the first end has a set-screw-receiving aperture configured to receive a set screw such that the first end is slideably engaged to the "C"-shaped central part and such that the occiput attachment is secured to the occi-cervical base member at any position among an infinite number of positions along length of the occi-cervical base member;
    a first polyaxial screw head adapted to be implanted in a first occipital condyle of the patient; and
    a second polyaxial screw head adapted to be implanted in a second occipital condyle of the patient;
    said first and second polyaxial screw heads adapted to engage first and second stabilizing rods, respectively, that are placed in-line with the cervical spine of a patient;
    said first and second polyaxial screw heads also adapted to engage said first and second attachment rods, respectively, said first and second attachment rods being disposed at a ninety degree (90°) angle relative to said first and second stabilizing rods.

2. The apparatus of claim 1, wherein upon engagement of said first and second attachment rods and the first and second stabilizing rods, occipito-cervical fusion employing fixation of the occipital condyle that incorporates the occipital bone and the C1/C2 levels is achieved.

3. The apparatus of claim 1, whereby hardware failure due to poor occipital bone purchase and limited points of fixation with occipital bone screws obtained is prevented.

4. The apparatus of claim 1, further comprising:
    a first saddle that accommodates and secures both the first stabilizing rod and said first attachment rod within said first polyaxial screw head; and
    a second saddle that accommodates and secures both the second stabilizing rod and said second attachment rod within said second polyaxial screw head.

5. An apparatus for stabilization of a patient's head relative to the patient's neck joint, comprising:
    an occi-cervical base member having a "C"-shaped central part that includes a pair of transversely spaced apart free ends;
    an occiput attachment having a first end engaged to the "C"-shaped central part and a flat, straight second end that extends radially outwardly relative to the first end;
    wherein the first end has a set-screw-receiving aperture configured to receive a set screw such that the first end is slideably engaged to the "C"-shaped central part and such that the occiput attachment is secured to the occi-cervical base member at any position among an infinite number of positions along length of the occi-cervical base member;
    a first attachment rod connected to and extending transversely from a first free end of the pair of free ends;
    a second attachment rod connected to and extending transversely from a second free end of the pair of free ends;
    a first polyaxial screw head adapted to be implanted in a first occipital condyle of a patient;
    a second polyaxial screw head adapted to be implanted in a second occipital condyle of a patient;
    each of said polyaxial screw heads having two grooves disposed at a ninety degree (90°) angle relative to one another, wherein said first and second polyaxial screw heads are also adapted to engage said first and second attachment rods, respectively.

6. The apparatus of claim 5, further comprising:
    said two grooves including a first groove that is deeper than a second groove;
    said first groove adapted to accommodate a first stabilizing rod that is placed in-line with a cervical spine;
    said second groove adapted to accommodate one of said attachment rods.

7. The apparatus of claim 6, further comprising:
    a saddle that accommodates and secures both the first stabilizing rod and the one of said attachment rods.

8. The apparatus of claim 1, wherein said first and second attachment rods are rigid.

9. The apparatus of claim 1, wherein said first and second attachment rods are polyaxial.

10. The apparatus of claim 9, further comprising:
    a plurality of locking set screws to secure said polyaxial first and second attachment rods in a preselected configuration.

11. The apparatus of claim 1, wherein said flat second end of said occiput attachment has at least one aperture, wherein said at least one aperture is adapted to receive a screw that secures said occiput attachment to the patient's occiput.

12. The apparatus of claim 1, further comprising a second occiput attachment having a first end slideably engaged to said "C"-shaped central part, and a flat, straight, second end that extends radially outwardly relative to said first end.

* * * * *